United States Patent [19]

Samreth et al.

[11] Patent Number: 5,169,838
[45] Date of Patent: Dec. 8, 1992

[54] BENZOPYRANONE-β-D-THIOXYLOSIDES AND THEIR USE IN THERAPY

[75] Inventors: Soth Samreth, Longvic; Véronique Barberousse, Dijon; Patrice Renaut, Hauteville - Les Dijon; Francois Bellamy, Saulon La Rue; Jean Millet, Corcelles les Citeaux, all of France

[73] Assignee: Fournier Industrie et Sante, Paris, France

[21] Appl. No.: 579,702

[22] Filed: Sep. 10, 1990

[30] Foreign Application Priority Data

Sep. 22, 1989 [FR] France .................................. 8912452
Mar. 16, 1990 [FR] France .................................. 9003401

[51] Int. Cl.⁵ ...................... A61K 31/70; C07H 15/24
[52] U.S. Cl. ........................................ 514/27; 536/4.1; 536/18.1; 536/122; 514/25
[58] Field of Search ...................... 536/4.1, 122, 18.1; 514/25, 27

[56] References Cited

FOREIGN PATENT DOCUMENTS

| | | |
|---|---|---|
| 0051023 | 5/1982 | European Pat. Off. . |
| 0130833 | 1/1985 | European Pat. Off. . |
| 0133103 | 2/1985 | European Pat. Off. . |
| 0221293 | 5/1987 | European Pat. Off. . |
| 0290321 | 11/1988 | European Pat. Off. . |
| 2100884 | 3/1972 | France . |

Primary Examiner—Johnnie R. Brown
Assistant Examiner—Elli Peselev
Attorney, Agent, or Firm—Jacobson, Price, Holman & Stern

[57] ABSTRACT

The present invention relates, by way of novel industrial products which are useful in therapy, to the benzopyranone-β-D-thioxyloside compounds of the formula

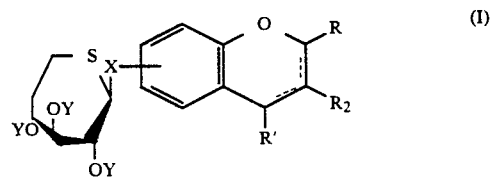

in which:
one of the substituents R or R' is an oxygen atom double-bonded to the corresponding cyclic carbon atom and the other is a group $R_1$,
the symbol represents a double bond conjugated to the CO group provided by one of the substituents R or R',
X is a sulfur atom or an oxygen atom,
$R_1$ and $R_2$, which are identical or different, are each a hydrogen atom, a $C_1$-$C_4$ alkyl group, a halogen atom, a trifluoromethyl group or a phenyl group, it being possible for $R_1$ and $R_2$, taken together, to form a 7,8,9,10-tetrahydrodibenzo[b,d]pyran-6-one group or a 1,2,3,4-tetrahydro-9H-xanthen-9-one group with the benzopyranone group to which they are bonded, and
Y is the hydrogen atom or an aliphatic acyl group.

10 Claims, No Drawings

BENZOPYRANONE-β-D-THIOXYLOSIDES AND THEIR USE IN THERAPY

The present invention relates, by way of novel industrial products, to the benzopyranone-β-D-thioxyloside compounds of formula I below. It further relates to their method of preparation and to their use in therapy as venous antithrombotics.

EP-B-0 051 023 has already disclosed benzoylphenyloside and α-hydroxybenzylphenyloside derivatives as ulcer inhibitors, platelet aggregation inhibitors, antithrombotics and cerebral oxygenators.

Also, EP-A-0 133 103 has disclosed benzylphenylosides which are useful as hypocholesterolemics and hypolipidemics, some of these compounds, in particular the product of Example 1, having antithrombotic effects as well.

Finally, EP-A-0 290 321 has disclosed benzoylphenylthioxyloside, α-hydroxybenzylphenylthioxyloside and benzylphenylthioxyloside derivatives as antithrombotics.

It has now just been found that the benzopyranone-β-D-thioxyloside compounds according to the invention, which are structurally different from the known products of the prior art, are useful in the treatment and prevention of diseases associated with circulatory disorders, especially as venous antithrombotics.

The novel products according to the invention are selected from the group consisting of the benzopyranone-β-D-thioxylosides of the formula

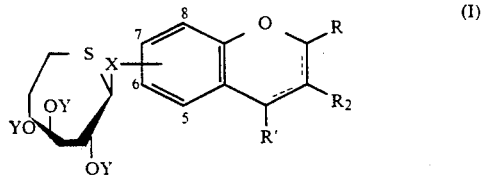

in which:
one of the substituents R or R' is an oxygen atom double-bonded to the corresponding cyclic carbon atom and the other is a group $R_1$,
the symbol ---- represents a double bond conjugated to the CO group provided by one of the substituents R or R',
X is a sulfur atom or an oxygen atom,
$R_1$ and $R_2$, which are identical or different, are each a hydrogen atom, a $C_1$-$C_4$ alkyl group, a halogen atom, a trifluoromethyl group or a phenyl group, it being possible for $R_1$ and $R_2$, taken together, to form a 7,8,9,10-tetrahydrodibenzo[b,d]pyran-6-one group or a 1,2,3,4-tetrahydro-9H-xanthen-9-one group with the benzopyranone group to which they are bonded,
the 5-, 6-, 7- and 8-positions are positions where the atom X can be bonded to the benzopyranone ring, and
Y is the hydrogen atom or an aliphatic acyl group.

In other words, the novel products according to the invention are selected from the group consisting of the compounds of the formulae

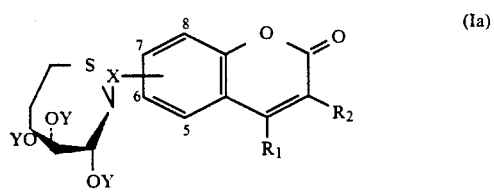

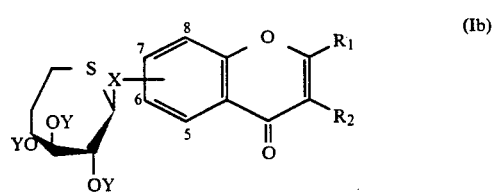

in which X, $R_1$, $R_2$ and Y are as defined above.

The preferred compounds according to the invention are the products of formula I in which X is bonded in the 7-position to the benzopyranone ring and in which $R_1$ and $R_2$, which are identical or different, are each a hydrogen atom, a $C_1$-$C_4$ alkyl group, a halogen atom or a phenyl group.

Among the aliphatic acyl groups which are suitable according to the invention, there may be mentioned those which contain a total of 2 to 5 carbon atoms, the preferred aliphatic acyl group being $CH_3CO$.

$C_1$-$C_4$ alkyl group is understood here as meaning a linear or branched hydrocarbon radical containing 1 to 4 carbon atoms, the preferred alkyl group being the methyl group.

Halogen atom is understood here as meaning a chlorine, fluorine or bromine atom, the preferred halogen atom being the chlorine atom.

The compounds of formula I and the corresponding acylated compounds can be prepared by means of a glycosylation reaction which comprises:
(i) reacting a compound of the formula

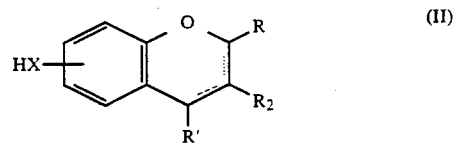

in which X, R, R' and $R_2$ are as defined above, with a thioxylose derivative selected from the group consisting of:
(i) the acylthioxylosyl halides of the formula

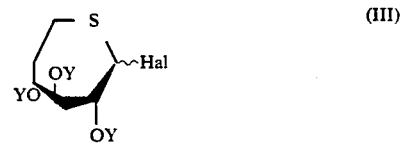

(ii) the peracylated thioxyloses of the formula

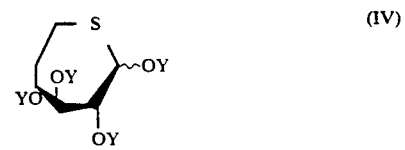

and (iii) the acylthioxylosyl trichloroacetimidates of the formula

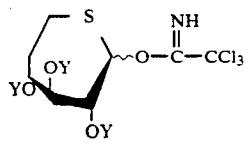 (V)

in which Hal is a halogen atom such as Cl or Br (the bromine atom being the preferred halogen atom here) and Y is an acyl group, especially an aliphatic acyl group containing a total of 2 to 5 carbon atoms and preferably the acetyl group, in an inert solvent, at a rate of 1 mol of II to about 0.6 to 1.2 mol of compound III, IV or V, especially in the presence of an acid acceptor and/or a Lewis acid, and (ii) if necessary, subjecting the resulting compound of formula I in which Y is a $C_2$-$C_5$ acyl group to a deacylation reaction at a temperature of between 0° C. and the reflux temperature of the reaction medium, in a $C_1$-$C_4$ lower alcohol (preferably methanol), in the presence of a metal alcoholate (preferably magnesium methylate or sodium methylate), to give a compound of formula I in which Y is H.

Compounds III, IV and V can be in the $\alpha$ or $\beta$ configuration or in the form of an anomeric mixture of both configurations.

The glycosylation reactions of the compounds of formula II were carried out either starting from compound III in the presence of a catalyst such as salts or oxides of silver, mercury or zinc, or starting from compound V in the presence of a Lewis acid, especially boron trifluoride etherate or zinc chloride, or starting from compound IV in the presence of a Lewis acid.

According to one preferred mode of carrying out the invention, it is recommended to condense 1 mol of the compound of formula II with about 1.1 to 1.2 mol of acylthioxylosyl halide III in an inert solvent selected from polar or apolar solvents (such as, for example, dimethylformamide, tetrahydrofuran, dioxane, acetonitrile, nitromethane, benzene, toluene, xylenes and mixtures thereof), in the presence of mercuric cyanide.

It will be advantageous to use 2,3,4-tri-O-acetyl-5-thio-D-xylopyranosyl bromide in a benzene/nitromethane mixture (1/1 v/v) or dichloroethane, in the presence of 1.1 to 1.3 mol of mercuric cyanide, at a temperature of between 0° C. and the reflux temperature of the reaction medium, preferably at about 40°-50° C., for 1 hour to 4 days.

According to a second preferred mode of carrying out the invention, it is recommended to condense 1 mol of the compound of formula II with about 1.1 to 1.2 mol of acylthioxylosyl halide III in an inert solvent (such as, for example, methylene chloride or acetonitrile), in the presence of silver imidazolate and zinc chloride.

It will be advantageous to use 2,3,4-tri-O-acetyl-5-thio-D-xylopyranosyl bromide in methylene chloride or a methylene chloride/acetonitrile mixture, in the presence of 1.5 to 1.7 mol of silver imidazolate and 2 to 2.2 mol of zinc chloride, at a temperature of between 0° C. and the reflux temperature of the reaction medium, preferably at about 40°-60° C., for 24 to 48 hours.

According to a third preferred mode of carrying out the invention, it is recommended to condense 1 mol of the compound of formula II with about 0.6 to 1 mol of acylthioxylosyl halide III in an inert solvent (such as, for example, toluene and/or acetonitrile), in the presence of zinc oxide.

It will be advantageous to use 2,3,4-tri-O-acetyl-5-thio-D-xylopyranosyl bromide in a toluene/acetonitrile mixture, in the presence of 0.5 to 1.2 mol of zinc oxide, at a temperature between room temperature and the reflux temperature of the reaction medium, preferably at about 40°-60° C., for 18 to 48 hours.

According to a fourth preferred mode of carrying out the invention, it is recommended to condense 1 mol of the compound of formula II with about 1.1 to 1.3 mol of acylthioxylosyl trichloroacetimidate in an inert solvent (such as, for example, methylene chloride or acetonitrile), in the presence of boron trifluoride etherate or zinc chloride.

It will be advantageous to use 2,3,4-tri-O-acetyl-5-thio-$\alpha$-D-xylopyranosyl trichloroacetimidate in methylene chloride, in the presence of 0.1 to 0.4 mol of boron trifluoride etherate dissolved in methylene chloride or acetonitrile, or in the presence of zinc chloride, at a temperature of between $-40°$ C. and room temperature (15°-25° C.), preferably at about $-20°$ C. to 0° C., for 1 to 5 hours.

In all cases the glycosylation reaction yields a mixture of the isomers of $\alpha$ and $\beta$ configuration in variable proportions.

The isomer of $\beta$ configuration is isolated by the methods known to those skilled in the art, such as, for example, fractional crystallization or chromatography, especially flash chromatography [i.e. chromatography on a silica column, under pressure, according to the technique described by W. C. STILL et al. in J. Org. Chem. (1978), 42 (No. 14) 2923].

Where appropriate, the derivatives obtained are subjected to deacylation, more particularly to deacetylation, which is carried out at a temperature of between 0° C. and the reflux temperature of the reaction medium, in a $C_1$-$C_4$ lower alcohol, in the presence of the corresponding metal alcoholate. Preferably, methanol will be chosen as the lower alcohol and sodium or magnesium methylate as the metal alcoholate.

If desired, the deacylation reaction can be carried out after glycosylation without isolation of the intermediate acylated compound formed.

It is also possible to carry out the deacylation reaction by an enzymatic method, for example with pork liver esterase.

To obtain the intermediates of formula II in which X=S, it is recommended to:

(i) condense dimethylaminothiocarbamoyl chloride of the formula

 (VI)

in a strong basic medium with a compound of the formula

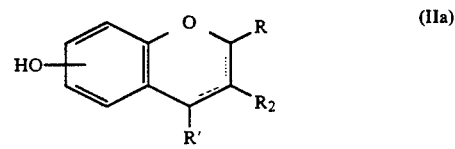 (IIa)

in which R, R' and R₂ are as defined above, to give a compound of the formula

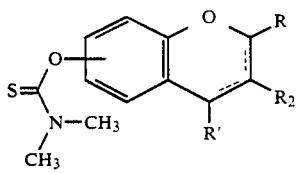

(VII)

in which R, R' and R₂ are as defined above, (ii) subject the resulting compound of formula VII to a Newmann rearrangement (J. Org. Chem. (1966) 31, p. 3980), by heating, to give a compound of the formula

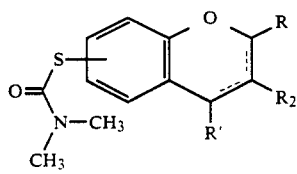

(VIII)

in which R, R' and R₂ are as defined above, and (iii) treat the resulting compound of formula VIII with a metal alcoholate, preferably sodium or magnesium methylate, in a $C_1$-$C_4$ lower alcohol, preferably methanol, dimethylformamide or dioxane, to give a compound of formula II in which X=S.

The intermediates of formula II in which X=S, R is an oxygen atom double-bonded to the corresponding cyclic carbon atom, R' is a group $R_1$ and the symbol ===== represents a double bond conjugated to the CO group provided by the substituent R can also be obtained by the nucleophilic substitution of an appropriate halogenobenzopyran-2-one compound according to the method described by L. TESTAFERRI in Tetrahedron Letters, vol. 21, p. 3099–3100 (1980).

The intermediate 2-ethyl-7-hydroxy-4H-1-benzopyran-4-one is a novel compound and forms one of the subjects of the invention.

The intermediates of formula II in which X=S are novel compounds with the exception of 7-mercapto-3-phenyl-2H-1-benzopyran-2-one, which is described in GB-A-1154272.

The compounds of the formula

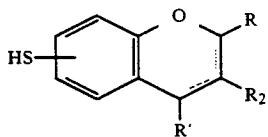

(IIb)

in which:
one of the substituents R or R' is an oxygen atom double-bonded to the corresponding cyclic carbon atom and the other is a group $R_1$,
the symbol ===== represents a double bond conjugated to the CO group provided by one of the substituents R or R',
$R_1$ and $R_2$, which are identical or different, are each a hydrogen atom, a $C_1$-$C_4$ alkyl group, a halogen atom, a trifluoromethyl group or a phenyl group, with the exception of the 3-phenyl group when R is an oxygen atom double-bonded to the corresponding cyclic carbon atom, R' is the hydrogen atom, the SH group is bonded in the 7-position and the symbol ===== represents a double bond conjugated to the CO group provided by the substituent R, it being possible for $R_1$ and $R_2$, taken together, to form a 7,8,9,10-tetrahydrodibenzo[b,d]pyran-6-one group or a 1,2,3,4-tetrahydro-9H-xanthen-9-one group with the benzopyranone group to which they are bonded, and the 5-, 6-, 7- and 8-positions are the positions in which the sulfur atom can be bonded to the benzopyranone ring, therefore form a further subject of the invention.

The intermediates of formula VIII are novel compounds.

The compounds of the formula

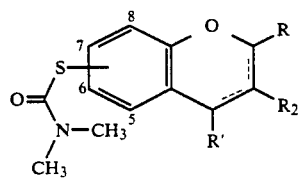

(VIII)

in which:
$R_1$ and $R_2$, which are identical or different, are each a hydrogen atom, a $C_1$-$C_4$ alkyl group, a halogen atom, a trifluoromethyl group or a phenyl group, it being possible for $R_1$ and $R_2$, taken together, to form a 7,8,9,10-tetrahydrodibenzo[b,d]pyran-6-one group or a 1,2,3,4-tetrahydro-9H-xanthen-9-one group with the benzopyranone to which they are bonded, and the 5-, 6-, 7- and 8-positions are the positions in which the sulfur atom can be bonded to the benzopyranone ring, therefore form a further subject of the invention.

According to the invention, a therapeutic composition is proposed which contains, in association with a physiologically acceptable excipient, at least one compound selected from the group consisting of the products of formula I. Of course, in such a composition, the active ingredient is present in a therapeutically effective amount.

The compounds of formula I are useful in therapy as antithrombotics. They are particularly useful in the prevention and treatment of disorders of the venous circulation.

According to the invention, it is recommended to use a substance belonging to the group consisting of the compounds of formula I in order to obtain an antithrombotic drug for use in therapy to combat disorders of the venous circulation.

Further characteristics and advantages of the invention will be understood more clearly from the following description of Preparatory Examples, which in no way imply a limitation and are given by way of illustration, and results of pharmacological tests.

In the following Preparatory Examples, the α or β configuration has been specified in the compound names in cases where said configuration was determined. Where the configuration is not indicated, this means that the corresponding product is an anomeric mixture of the α and β configurations in proportions which were not determined.

PREPARATION I

Preparation of 4-ethyl-2-oxo-2H-1-benzopyran-7-yl 2,3,4-tri-O-acetyl-5-thio-β-D-xylopyranoside (Example 1a)

A suspension of 2.28 g ($12.10^{-3}$ mol) of 4-ethyl-7-hydroxy-2H-1-benzopyran-2-one, 4.7 g ($13.2.10^{-3}$ mol) of 2,3,4-tri-O-acetyl-5-thio-D-xylopyranosyl bromide and a 0.4 nm molecular sieve in 125 ml of toluene and 120 ml of acetonitrile is stirred in the presence of 3.28 g ($24.10^{-3}$ mol) of zinc chloride and 4.2 g ($14.10^{-3}$ mol) of silver imidazolate, in the absence of light, under an inert atmosphere. After heating at 55° C. for 24 h, the reaction mixture is filtered on Célite ® (i.e. diatomaceous silica for filtration) in ethyl acetate. The filtrate is washed with a 1N solution of hydrochloric acid, a 1N solution of sodium hydroxide and then a saturated solution of sodium chloride and dried over magnesium sulfate and the solvents are evaporated off under reduced pressure. After purification by chromatography on silica gel using an ethyl acetate/toluene mixture (1/6 v/v) as the eluent, and precipitation in ether, 0.93 g (yield: 17%) of the expected product is obtained.

M.p.=189° C.
$[\alpha]_D^{20} = -73.8°$ (c=0.25; CHCl$_3$)

The following products were prepared by an analogous procedure: 4-methyl-2-oxo-2H-1-benzopyran-6-yl 2,3,4-tri-O-acetyl-5-thio-β-D-xylopyranoside (Example 2a)

M.p.=179°-184° C.
$[\alpha]_D^{20} = -47.9°$ (c=0.33; CHCl$_3$)

4-trifluoromethyl-2-oxo-2H-1-benzopyran-7-yl 2,3,4-tri-O-acetyl-5-thio-β-D-xylopyranoside (Example 3a)

M.p.=184° C.
$[\alpha]_D^{20} = +29.2°$ (c=0.55; CHCl$_3$)

4-methyl-2-oxo-2H-1-benzopyran-8-yl 2,3,4-tri-O-acetyl-5-thio-β-D-xylopyranoside (Example 4a)

M.p.=220°-223° C.
$[\alpha]_D^{23} = -121.9°$ (c=0.21; CHCl$_3$)

2-oxo-4-propyl-2H-1-benzopyran-7-yl 2,3,4-tri-O-acetyl-5-thio-β-D-xylopyranoside (Example 5a)

M.p.=165°-167° C.
$[\alpha]_D^{20} = -71.2°$ (c=0.11; CHCl$_3$)

4-methyl-2-oxo-2H-1-benzopyran-5-yl 2,3,4-tri-O-acetyl-5-thio-β-D-xylopyranoside (Example 6a)

M.p.=167° C.
$[\alpha]_D^{22} = -81°$ (c=0.15; CHCl$_3$)

4-methyl-2-oxo-2H-1-benzopyran-7-yl 2,3,4-tri-O-acetyl-5-thio-β-D-xylopyranoside (Example 16a)

M.p.=193° C.
$[\alpha]_D^{20} = -72°$ (c=0.5; CHCl$_3$)

3-chloro-4-methyl-2-oxo-2H-1-benzopyran-7-yl 2,3,4-tri-O-acetyl-5-thio-β-D-xylopyranoside (Example 17a)

M.p.=227° C.
$[\alpha]_D^{20} = -50.7°$ (c=0.27; CHCl$_3$)

4-methyl-2-oxo-3-phenyl-2H-1-benzopyran-7-yl 2,3,4-tri-O-acetyl-5-thio-β-D-xylopyranoside (Example 18a)

M.p.=210° C.
$[\alpha]_D^{27.5} = -56.5°$ (c=0.1; CHCl$_3$)

4-(1-methylethyl)-2-oxo-2H-1-benzopyran-7-yl 2,3,4-tri-O-acetyl-5-thio-β-D-xylopyranoside (Example 19a)

M.p.=144°-145° C.
$[\alpha]_D^{30} = -26.4°$ (c=0.1; CH$_3$OH)

2-methyl-4-oxo-4H-1-benzopyran-7-yl 2,3,4-tri-O-acetyl-5-thio-β-D-xylopyranoside (Example 20a)

M.p.=188° C.
$[\alpha]_D^{23} = -77.4°$ (c=0.47; CHCl$_3$)

2-ethyl-4-oxo-4H-1-benzopyran-7-yl 2,3,4-tri-O-acetyl-5-thio-β-D-xylopyranoside (Example 21a)

M.p.=150°-151° C.
$[\alpha]_D^{21} = -64°$ (c=0.54; CHCl$_3$)

2,3-dimethyl-4-oxo-4H-1-benzopyran-7-yl 2,3,4-tri-O-acetyl-5-thio-β-D-xylopyranoside (Example 22a)

M.p.=203°-205° C.
$[\alpha]_D^{21} = -65°$ (c=0.6; CHCl$_3$)

2-methyl-4-oxo-4H-1-benzopyran-6-yl 2,3,4-tri-O-acetyl-5-thio-β-D-xylopyranoside (Example 24a)

M.p.=168°-180° C.
$[\alpha]_D^{25} = -81.9°$ (c=0.3; CHCl$_3$)

4-oxo-2-phenyl-4H-1-benzopyran-7-yl 2,3,4-tri-O-acetyl-5-thio-β-D-xylopyranoside (Example 25a)

M.p.=215° C.
$[\alpha]_D^{24} = -62°$ (c=0.51; CHCl$_3$)

3-bromo-2-methyl-4-oxo-4H-1-benzopyran-7-yl 2,3,4-tri-O-acetyl-5-thio-β-D-xylopyranoside (Example 28a)

M.p.=192°-194° C.
$[\alpha]_D^{21} = -54°$ (c=0.54; CHCl$_3$)

PREPARATION II

Preparation of 4-methyl-2-oxo-2H-1-benzopyran-5-yl 2,3,4-tri-O-acetyl-1,5-dithio-β-D-xylopyranoside (Example 7a)

A suspension of 420 mg ($2.2.10^{-3}$ mol) of 5-mercapto-4-methyl-2H-1-benzopyran-2-one, 970 mg ($2.7.10^{-3}$ mol) of 2,3,4-tri-O-acetyl-5-thio-D-xylopyranosyl bromide, 550 mg ($2.2.10^{-3}$ mol) of mercuric cyanide and a 0.4 nm molecular sieve in 50 ml of nitromethane and 50 ml of benzene is stirred at 45° C. under an inert atmosphere for 24 h. The reaction mixture is then filtered on Célite ® in ethyl acetate. The filtrate is washed with a 1N solution of hydrochloric acid, a 1N solution of sodium hydroxide and then a saturated solution of sodium chloride, dried over magnesium sulfate and evaporated under reduced pressure. After purification by chromatography on silica gel using an ethyl acetate/toluene mixture (1/5 v/v) as the eluent, and then precipitation in ether, 250 mg (yield: 25%) of the expected product are obtained.

M.p.=187° C.
$[\alpha]_D^{22} = +34.5°$ (c=0.11; CHCl$_3$)

The following products were prepared by an analogous procedure:

4-methyl-2-oxo-2H-1-benzopyran-8-yl 2,3,4-tri-O-acetyl-1,5-dithio-β-D-xylopyranoside (Example 9a)

M.p.=205° C.
$[\alpha]_D^{23} = +86.25°$ (c=0.3; CHCl$_3$)

4-methyl-2-oxo-2H-1-benzopyran-6-yl 2,3,4-tri-O-acetyl-1,5-dithio-β-D-xylopyranoside (Example 10a)

M.p.=139°-140° C.
$[\alpha]_D^{23} = -66.13°$ (c=0.3; CHCl$_3$)

7,8,9,10-tetrahydro-6-oxo-6H-dibenzo[b,d]pyran-3-yl 2,3,4-tri-O-acetyl-1,5-dithio-β-D-xylopyranoside (Example 15a)

M.p.=191° C.
$[\alpha]_D^{23} = +14.5°$ (c=0.3; CHCl$_3$)

2-methyl-4-oxo-4H-1-benzopyran-7-yl 2,3,4-tri-O-acetyl-1,5-dithio-β-D-xylopyranoside (Example 23a)

M.p.=171° C.
$[\alpha]_D^{21} = +54.3°$ (c=0.14; CHCl$_3$)

2,3-dimethyl-4-oxo-4H-1-benzopyran-7-yl 2,3,4-tri-O-acetyl-1,5-dithio-β-D-xylopyranoside (Example 26a)

M.p.=169°-173° C.
$[\alpha]_D^{30} = +55.5°$ (c=0.38; CHCl$_3$)

2-ethyl-4-oxo-4H-1-benzopyran-7-yl 2,3,4-tri-O-acetyl-1,5-dithio-β-D-xylopyranoside (Example 27a)

M.p.=85°-90° C.
$[\alpha]_D^{20} = +58°$ (c=0.5; CHCl$_3$)

PREPARATION III

Preparation of 4-methyl-2-oxo-2H-1-benzopyran-7-yl 2,3,4-tri-O-acetyl-1,5-dithio-β-D-xylopyranoside (Example 8a)

A mixture of 8 g (41.6.10$^{-3}$ mol) of 7-mercapto-4-methyl-2H-1-benzopyran-2-one, 17.7 g (50.10$^{-3}$ mol) of 2,3,4-tri-O-acetyl-5-thio-α-D-xylopyranosyl bromide and 3.4 g (42.10$^{-3}$ mol) of zinc oxide in 180 ml of toluene and 180 ml of acetonitrile is heated for 12 hours at 45° C. After filtration on Célite ® and washing of the resulting residue with ethyl acetate, the organic phase is washed with a 1N solution of hydrochloric acid, then a 1N solution of sodium hydroxide and finally a saturated solution of sodium chloride. The organic phase obtained is dried over magnesium sulfate and evaporated under reduced pressure. After precipitation by the addition of ethyl ether, 14.2 g (yield: 73%) of a yellow powder are obtained.

M.p.=168° C.
$[\alpha]_D^{22} = 46.4°$ (c=0.7; CHCl$_3$)

The following products were prepared by an analogous procedure:

4-trifluoromethyl-2-oxo-2H-1-benzopyran-7-yl 2,3,4-tri-O-acetyl-1,5-dithio-β-D-xylopyranoside (Example 11a)

M.p.=184° C.
$[\alpha]_D^{23} = +80.25°$ (c=0.5; CHCl$_3$)

3-chloro-4-methyl-2-oxo-2H-1-benzopyran-7-yl 2,3,4-tri-O-acetyl-1,5-dithio-β-D-xylopyranoside (Example 12a)

M.p.=160°-162° C.
$[\alpha]_D^{23} = +70.2°$ (c=0.5; CHCl$_3$)

4-ethyl-2-oxo-2H-1-benzopyran-7-yl 2,3,4-tri-O-acetyl-1,5-dithio-β-D-xylopyranoside (Example 13a)

M.p.=153° C.
$[\alpha]_D^{23} = +28.11°$ (c=0.5; CHCl$_3$)

2-oxo-4-propyl-2H-1-benzopyran-7-yl 2,3,4-tri-O-acetyl-1,5-dithio-β-D-xylopyranoside (Example 14a)

M.p.=137° C.
$[\alpha]_D^{23} = +31.17°$ (c=0.5; CHCl$_3$)

PREPARATION IV

Preparation of 4-ethyl-2-oxo-2H-1-benzopyran-7-yl 5-thio-β-D-xylopyranoside (Example 1)

60 μl of sodium methylate (8%.of Na (w/v) in methanol) are added to a solution of 0.45 g (0.97.10$^{-3}$ mol) of 4-ethyl-2-oxo-2H-1-benzopyran-7-yl 2,3,4-tri-O-acetyl-5-thio-β-D-xylopyranoside in 5 ml of methanol. After stirring for 24 h at room temperature, the reaction medium is neutralized by the addition of Amberlite ® IR 120H+ resin, solubilized with tetrahydrofuran, filtered and treated with animal charcoal. The solvents are evaporated off under reduced pressure and 0.285 g (yield: 87%) of the expected product is then obtained after lyophilization.

M.p.=192° C.
$[\alpha]_D^{20} = -69°$ (c=0.21; dimethyl sulfoxide)

The following products were prepared by an analogous procedure:

4-methyl-2-oxo-2H-1-benzopyran-6-yl 5-thio-β-D-xylopyranoside (Example 2)

M.p.=109°-113° C.
$[\alpha]_D^{20} = -63.3°$ (c=0.24; dimethyl sulfoxide)

4-trifluoromethyl-2-oxo-2H-1-benzopyran-7-yl
5-thio-β-D-xylopyranoside (Example 3)

M.p.=210°-213° C.
$[\alpha]_D^{20}= +34.1°$ (c=0.5; CH₃OH)

4-methyl-2-oxo-2H-1-benzopyran-8-yl
5-thio-β-D-xylopyranoside (Example 4)

M.p.=120°-125° C.
$[\alpha]_D^{20}= -16°$ (c=0.12; dimethyl sulfoxide)

2-oxo-4-propyl-2H-1-benzopyran-7-yl
5-thio-β-D-xylopyranoside (Example 5)

M.p.=192° C.
$[\alpha]_D^{24}= -61.3°$ (c=0.15; dimethyl sulfoxide)

4-methyl-2-oxo-2H-1-benzopyran-5-yl
5-thio-β-D-xylopyranoside (Example 6)

M.p.=184°-188° C.
$[\alpha]_D^{23}= -85.2°$ (c=0.11; dimethyl sulfoxide)

4-methyl-2-oxo-2H-1-benzopyran-5-yl
1,5-dithio-β-D-xylopyranoside (Example 7)

M.p.=203° C.
$[\alpha]_D^{22}= +28.3°$ (c=0.12; CH₃OH)

4-methyl-2-oxo-2H-1-benzopyran-7-yl
1,5-dithio-β-D-xylopyranoside (Example 8)

M.p.=216° C.
$[\alpha]_D^{23}= -19.4°$ (c=0.3; dimethyl sulfoxide)

4-methyl-2-oxo-2H-1-benzopyran-8-yl
1,5-dithio-β-D-xylopyranoside (Example 9)

M.p.=178° C.
$[\alpha]_D^{23}= -61.5°$ (c=0.2; dimethyl sulfoxide)

4-methyl-2-oxo-2H-1-benzopyran-6-yl
1,5-dithio-β-D-xylopyranoside (Example 10)

M.p.=182° C.
$[\alpha]_D^{20}= +6.9°$ (c=0.6; tetrahydrofuran)

4-trifluoromethyl-2-oxo-2H-1-benzopyran-7-yl
1,5-dithio-β-D-xylopyranoside (Example 11)

M.p.=178°-180° C.
$[\alpha]_D^{25}= +40.8°$ (c=0.26; CH₃OH)

3-chloro-4-methyl-2-oxo-2H-1-benzopyran-7-yl
1,5-dithio-β-D-xylopyranoside (Example 12)

M.p.=230° C.
$[\alpha]_D^{22}= +32.7°$ (c=0.3; dimethyl sulfoxide)

4-ethyl-2-oxo-2H-1-benzopyran-7-yl
1,5-dithio-β-D-xylopyranoside (Example 13)

M.p.=184° C.
$[\alpha]_D^{25}= +0.6°$ (c=0.3; tetrahydrofuran)

2-oxo-4-propyl-2H-1-benzopyran-7-yl
1,5-dithio-β-D-xylopyranoside (Example 14)

M.p.=176°-178° C.
$[\alpha]_D^{25}= +3.0°$ (c=0.3; tetrahydrofuran)

7,8,9,10-tetrahydro-6-oxo-6H-dibenzo[b,d]pyran-3-yl
1,5-dithio-β-D-xylopyranoside (Example 15)

M.p.=182°-183° C.
$[\alpha]_D^{22}= +20.6°$ (c=0.3; dimethyl sulfoxide)

4-methyl-2-oxo-2H-1-benzopyran-7-yl
5-thio-β-D-xylopyranoside (Example 16)

M.p.=190°-206° C.
$[\alpha]_D^{20}= -72°$ (c=0.5; dimethyl sulfoxide)

3-chloro-4-methyl-2-oxo-2H-1-benzopyran-7-yl
5-thio-β-D-xylopyranoside (Example 17)

M.p.=208°-210° C.
$[\alpha]_D^{20}= -22.9°$ (c=0.24; dimethyl sulfoxide)

4-methyl-2-oxo-3-phenyl-2H-1-benzopyran-7-yl
5-thio-β-D-xylopyranoside (Example 18)

M.p.=188°-200° C.
$[\alpha]_D^{22}= -59.2°$ (c=0.12; CH₃OH)

4-(1-methylethyl)-2-oxo-2H-1-benzopyran-7-yl
5-thio-β-D-xylopyranoside (Example 19)

M.p.=186°-190° C.
$[\alpha]_D^{22}= -74.3°$ (c=0.14; CH₃OH)

2-methyl-4-oxo-4H-1-benzopyran-7-yl
5-thio-β-D-xylopyranoside (Example 20)

M.p.=193°-195° C.
$[\alpha]_D^{22}= -92°$ (c=0.5; methanol)

2-ethyl-4-oxo-4H-1-benzopyran-7-yl
5-thio-β-D-xylopyranoside (Example 21)

M.p.=130°-137° C.
$[\alpha]_D^{21}= -84°$ (c=0.54; methanol)

2,3-dimethyl-4-oxo-4H-1-benzopyran-7-yl
5-thio-β-D-xylopyranoside (Example 22)

M.p.=177°-194° C.
$[\alpha]_D^{21}= -88.6°$ (c=0.45; tetrahydrofuran)

2-methyl-4-oxo-4H-1-benzopyran-7-yl
1,5-dithio-β-D-xylopyranoside (Example 23)

M.p. = 194°-196° C.
$[\alpha]_D^{22} = +19.1°$ (c = 0.2; dimethyl sulfoxide)

2-methyl-4-oxo-4H-1-benzopyran-6-yl
5-thio-β-D-xylopyranoside (Example 24)

M.p. = 108° (decomposition: 200°-240° C.)
$[\alpha]_D^{25} = -107.7°$ (c = 0.3; methanol)

4-oxo-2-phenyl-4H-1-benzopyran-7-yl
5-thio-β-D-xylopyranoside (Example 25)

M.p. = 222° C.
$[\alpha]_D^{20} = -90°$ (c = 0.5; tetrahydrofuran)

2,3-dimethyl-4-oxo-4H-1-benzopyran-7-yl
1,5-dithio-β-D-xylopyranoside (Example 26)

M.p. = 204°-208° C.
$[\alpha]_D^{30} = +28.3°$ (c = 0.35; methanol)

2-ethyl-4-oxo-4H-1-benzopyran-7-yl
1,5-dithio-β-D-xylopyranoside (Example 27)

M.p. = 155° C.
$[\alpha]_D^{20} = +26.2°$ (c = 0.53; methanol)

3-bromo-2-methyl-4-oxo-4H-1-benzopyran-7-yl
5-thio-β-D-xylopyranoside (Example 28)

M.p. = 135°-138° C.
$[\alpha]_D^{21} = -43°$ (c = 0.5; dimethyl sulfoxide)

PREPARATION V

Preparation of
O-(4-methyl-2-oxo-2H-1-benzopyran-5-yl)
dimethylthiocarbamate 410 mg ($7.3.10^{-3}$ mol) of potassium hydroxide are added under an inert atmosphere to a suspension of 1 g ($5.7.10^{-3}$ mol) of 5-hydroxy-4-methyl-2H-1-benzopyran-2-one in 10 ml of water and 10 ml of acetone. After 10 minutes at room temperature, 770 mg ($6.2.10^{-3}$ mol) of dimethylthiocarbamoyl chloride in 10 ml of acetone are added at 0° C. The reaction mixture is stirred for 2 hours at room temperature and then, after evaporation of the acetone, the expected derivative is precipitated in water to give 1.35 g (yield: 90%) of the expected product.
M.p. = 166°-168° C.

The products collated in Tables III and IV below were prepared by an analogous procedure.

PREPARATION VI

Preparation of
S-(4-methyl-2-oxo-2H-1-benzopyran-5-yl)
dimethylthiocarbamate

A solution of 3.7 g ($14.10^{-3}$ mol) of O-(4-methyl-2-oxo-2H-1-benzopyran-5-yl) dimethylthiocarbamate in 50 ml of 1,2,3,4-tetrahydronaphthalene is kept at 220° C. for 14 hours. After cooling, the expected product is precipitated in ether. The crystals obtained are rinsed with cyclohexane to give 2.95 g (yield: 80%) of the expected product.
M.p. = 129° C.

The products collated in Tables V and VI below were prepared by an analogous procedure.

PREPARATION VII

Preparation of methyl
3-(2-hydroxy-6-(dimethylaminocarbonylthio)phenyl)-
but-2-enoate 4.4 ml of sodium methylate (8% of Na (w/v) in methanol) are added under an inert atmosphere to a solution of 2 g ($7.6.10^{-3}$ mol) of S-(4-methyl-2-oxo-2H-1-benzopyran-5-yl) dimethylthiocarbamate in 20 ml of methanol. After 4 hours at room temperature, the reaction medium is hydrolyzed in an ice/hydrochloric acid mixture and the precipitate formed is filtered off to give 1.7 g (yield: 76%) of the expected product.
M.p. = 152° C.

PREPARATION VIII

Preparation of
7-mercapto-4-methyl-2H-1-benzopyran-2-one 4 ml of sodium methylate (8% of Na (w/v) in methanol) are added at 60° C. to a solution of 1 g ($3.4.10^{-3}$ mol) of methyl 3-(2-hydroxy-6-(dimethylaminocarbonylthio)phenyl)but-2-enoate in 10 ml of anhydrous dimethylformamide. After 6 hours at 60° C., the reaction medium is hydrolyzed in a hydrochloric acid/ice mixture to give 0.550 g (yield: 85%) of the expected product.
M.p. = 136° C.

PREPARATION IX

Preparation of
7-mercapto-4-methyl-2H-1-benzopyran-2-one 26.3 g (0.1 mol) of S-(4-methyl-2-oxo-2H-1-benzopyran-7-yl) dimethylthiocarbamate are suspended in 300 ml of methanol under a nitrogen atmosphere. 0.2 mol of sodium methylate (8% solution of Na (w/v) in methanol) is added at room temperature and the mixture is heated at 45° C. for 4 hours. The disappearance of the starting material is monitored by thin layer chromatography using an ethyl acetate/toluene mixture (1/4 v/v) as the eluent. After cooling, the reaction medium is hydrolyzed on an ice/concentrated hydrochloric acid mixture and, after stirring for 30 minutes, the precipitate obtained is filtered off and then washed with water. After drying over P$_2$O$_5$, 19.2 g (yield ≈ 100%) of the expected product are obtained.
M.p. = 132° C.

The products collated in Tables VII and VIII below were prepared by an analogous procedure.

PREPARATION X

Preparation of
2-ethyl-7-(1-oxopropoxy)-3-(1-oxopropyl)-4H-1-benzopyran-4-one

A solution of 5 g ($32.2.10^{-3}$ mol) of 1-(2,4-dihydroxyphenyl)ethanone and 4 g ($48.8.10^{-3}$ mol) of sodium acetate in 40 ml of propionic anhydride is kept at a temperature of 170° C. under an inert atmosphere for 20 hours. The reaction mixture is hydrolyzed in the presence of sodium bicarbonate and the product is extracted with ethyl acetate and then washed with water. The organic phase obtained is dried over magnesium sulfate.

The solvent is evaporated off under reduced pressure. After the addition of toluene, the remaining solvents are evaporated off again under reduced pressure. After purification by chromatography on silica gel using a hexane/ethyl acetate mixture (6/1 v/v) as the eluent, 2 g (yield: 20%) of the expected product are obtained.

M.p. = 84° C.

PREPARATION XI

Preparation of 2-ethyl-7-hydroxy-4H-1-benzopyran-4-one

A suspension of 6.5 g ($21.5.10^{-3}$ mol) of 2-ethyl-7-(1-oxopropoxy)-3-(1-oxopropyl)-4H-1benzopyran-4-one and 5 g ($47.40^3$ mol) of sodium carbonate in 65 ml of water is kept at a temperature of 150° C. for 9 hours. The reaction mixture is hydrolyzed with a 1N solution of hydrochloric acid. The product is extracted with ethyl acetate. After purification by chromatography on silica gel using an ether/methylene chloride mixture (1/2 v/v) as the eluent, 2.45 g (yield: 61%) of the expected product are obtained.

M.p. = 189° C.

PREPARATION XII

Preparation of 7-acetyl-3-bromo-2-methyl-4H-1-benzopyran-4-one 77.5 ml of a 10% solution of bromine in acetic acid are added at 60° C., under an inert atmosphere, to a solution of 8.8 g ($40.10^{-3}$ mol) of 7-acetyl-2-methyl-4H-1-benzopyran-4-one in 80 ml of acetic acid. The reaction mixture is kept at 60° C. for 2 hours and is then left to stand for 12 hours. It is concentrated under reduced pressure and the residue is then neutralized with a saturated solution of sodium bicarbonate. After extraction with ethyl acetate, the organic phase is washed with water until the pH of the washings is neutral, dried over magnesium sulfate and concentrated to dryness. After chromatography on silica gel using a methylene chloride/methanol mixture (12/1 v/v) as the eluent, 2.3 g (yield: 19%) of the expected product are obtained.

M.p. = 124° C.

PREPARATION XIII

Preparation of 3-bromo-7-hydroxy-2-methyl-4H-1-benzopyran-4-one 2.2 ml of sodium methylate (8% of Na (w/v) in methanol) are added under an inert atmosphere to a suspension of 2.3 g ($7.7.10^{-3}$ mol) of 7-acetyl-3-bromo-2-methyl-4H-1-benzopyran-4-one in 40 ml of methanol. After 30 minutes, the reaction mixture is hydrolyzed with an iced solution of hydrochloric acid. The precipitate formed is filtered off and then washed until the pH of the washings is neutral. 1.9 g (yield: 96%) of the expected product are thus obtained.

M.p. = 305°–310° C. (decomposition)

Without implying a limitation, a number of compounds according to the invention have been collated in Tables I and II below.

The antithrombotic activity of the products according to the invention was demonstrated by means of the following operating protocol for venous thrombosis:

A venous stasis under hypercoagulation is produced according to the technique described by WESSLER et al. (J. Applied Physiol. 1959, p. 943–946). As in the technique described by J. HAUPMAN et al. (Thrombosis and Haemostasis 43(2), 1980, p. 118), the hypercoagulant used is a solution of activated factor X (Xa) supplied by Flow Laboratories (71 Knat per 12.5 ml of isotonic solution).

The study is performed on unfasted male Wistar rats weighing 250 to 280 g, divided up into groups of 10 animals each. The test products are administered orally as a suspension in PEG 400. A thrombosis is induced 4 hours after this treatment and the thrombus formed is removed and weighed.

The results obtained at a dose of 3 mg/kg, administered orally, have been collated in Tables I and II.

TABLE I

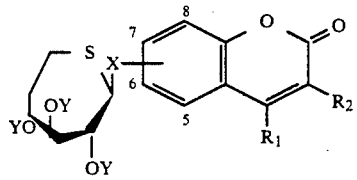

| Example | X | Position | $R_1$ | $R_2$ | Y | % inhibition at 3 mg/kg |
|---|---|---|---|---|---|---|
| 1a | O | 7 | —CH$_2$—CH$_3$ | —H | —COCH$_3$ | 65 |
| 1 | O | 7 | —CH$_2$—CH$_3$ | —H | —H | 87 |
| 2a | O | 6 | —CH$_3$ | —H | —COCH$_3$ | 53 |
| 2 | O | 6 | —CH$_3$ | —H | —H | 81 |
| 3a | O | 7 | —CF$_3$ | —H | —COCH$_3$ | 47 |
| 3 | O | 7 | —CF$_3$ | —H | —H | 80 |
| 4a | O | 8 | —CH$_3$ | —H | —COCH$_3$ | 51 |
| 4 | O | 8 | —CH$_3$ | —H | —H | 52 |
| 5a | O | 7 | —(CH$_2$)$_2$—CH$_3$ | —H | —COCH$_3$ | 46 |
| 5 | O | 7 | —(CH$_2$)$_2$—CH$_3$ | —H | —H | 26 |
| 6a | O | 5 | —CH$_3$ | —H | —COCH$_3$ | — |
| 6 | O | 5 | —CH$_3$ | —H | —H | 42 |
| 7a | S | 5 | —CH$_3$ | —H | —COCH$_3$ | — |
| 7 | S | 5 | —CH$_3$ | —H | —H | 38 |
| 8a | S | 7 | —CH$_3$ | —H | —COCH$_3$ | 65 |
| 8 | S | 7 | —CH$_3$ | —H | —H | 46 |
| 9a | S | 8 | —CH$_3$ | —H | —COCH$_3$ | — |
| 9 | S | 8 | —CH$_3$ | —H | —H | 31 |
| 10a | S | 6 | —CH$_3$ | —H | —COCH$_3$ | 32 |
| 10 | S | 6 | —CH$_3$ | —H | —H | 37 |
| 11a | S | 7 | —CF$_3$ | —H | —COCH$_3$ | — |

TABLE I-continued

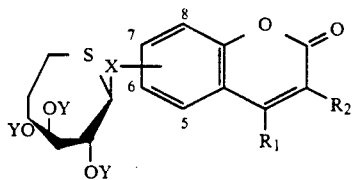

| Example | X | Position | R₁ | R₂ | Y | % inhibition at 3 mg/kg |
|---|---|---|---|---|---|---|
| 11 | S | 7 | —CF$_3$ | —H | —H | 36 |
| 12a | S | 7 | —CH$_3$ | —Cl | —COCH$_3$ | 32 |
| 12 | S | 7 | —CH$_3$ | —Cl | —H | 65 |
| 13a | S | 7 | —CH$_2$—CH$_3$ | —H | —COCH$_3$ | 58 |
| 13 | S | 7 | —CH$_2$—CH$_3$ | —H | —H | 54 |
| 14a | S | 7 | —(CH$_2$)$_2$—CH$_3$ | —H | —COCH$_3$ | 25 |
| 14 | S | 7 | —(CH$_2$)$_2$—CH$_3$ | —H | —H | 43 |
| 15a | S | 7 | —CH$_2$—CH$_2$—CH$_2$—CH$_2$— | | —COCH$_3$ | 23 |
| 15 | S | 7 | —CH$_2$—CH$_2$—CH$_2$—CH$_2$— | | —H | 31 |
| 16a | O | 7 | —CH$_3$ | —H | —COCH$_3$ | 63 |
| 16 | O | 7 | —CH$_3$ | —H | —H | 63 |
| 17a | O | 7 | —CH$_3$ | —Cl | —COCH$_3$ | 67 |
| 17 | O | 7 | —CH$_3$ | —Cl | —H | 64 |
| 18a | O | 7 | —CH$_3$ | phenyl | —COCH$_3$ | 20 |
| 18 | O | 7 | —CH$_3$ | phenyl | —H | 43 |
| 19a | O | 7 | —CH(CH$_3$)$_2$ | —H | —COCH$_3$ | — |
| 19 | O | 7 | —CH(CH$_3$)$_2$ | —H | —H | 36 |
| A | comparative product described in Example 1 of EP-A-0133103 | | | | | 14 (1) |
| B | comparative product described in Example 97 of EP-B-0051023 | | | | | 5.5 (1) |
| C | comparative product described in Example 3 of EP-A-0290321 | | | | | 20 (2) |

Notes:
(1) product tested at 12.5 mg/kg, administered orally
(2) product tested at 3 mg/kg, administered orally

TABLE II

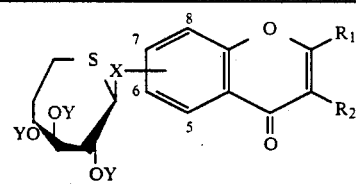

| Example n° | X | Position | Y | R₁ | R₂ | % inhibition at 3 mg/kg |
|---|---|---|---|---|---|---|
| 20a | O | 7 | —COCH$_3$ | —CH$_3$ | —H | 20 |
| 20 | O | 7 | —H | —CH$_3$ | —H | 53 |
| 21a | O | 7 | —COCH$_3$ | —C$_2$H$_5$ | —H | 42 |
| 21 | O | 7 | —H | —C$_2$H$_5$ | —H | 70 |
| 22a | O | 7 | —COCH$_3$ | —CH$_3$ | —CH$_3$ | 66 |
| 22 | O | 7 | —H | —CH$_3$ | —CH$_3$ | 36 |
| 23a | S | 7 | —COCH$_3$ | —CH$_3$ | —H | — |
| 23 | S | 7 | —H | —CH$_3$ | —H | 26 |
| 24a | O | 6 | —COCH$_3$ | —CH$_3$ | —H | — |
| 24 | O | 6 | —H | —CH$_3$ | —H | 36 |
| 25a | O | 7 | —COCH$_3$ | —C$_6$H$_5$ | —H | — |
| 25 | O | 7 | —H | —C$_6$H$_5$ | —H | 28 |
| 26a | S | 7 | —COCH$_3$ | —CH$_3$ | —CH$_3$ | — |
| 26 | S | 7 | —H | —CH$_3$ | —CH$_3$ | 27 |
| 27a | S | 7 | —COCH$_3$ | —C$_2$H$_5$ | —H | 23 |
| 27 | S | 7 | —H | —C$_2$H$_5$ | —H | 26 |
| 28a | O | 7 | —COCH$_3$ | —CH$_3$ | —Br | 25 |

TABLE II-continued

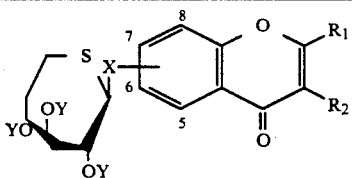

| Example n° | X | Position | Y | R₁ | R₂ | % inhibition at 3 mg/kg |
|---|---|---|---|---|---|---|
| 28 | O | 7 | —H | —CH$_3$ | —Br | 49 |
| A | comparative product described in Example 1 of EP-A-0133103 | | | | | 14 (1) |
| B | comparative product described in Example 97 of EP-B-0051023 | | | | | 5.5 (1) |
| C | comparative product described in Example 3 of EP-A-0290321 | | | | | 20 (2) |

Notes:
(1) product tested at 12.5 mg/kg, administered orally
(2) product tested at 3 mg/kg, administered orally

TABLE III

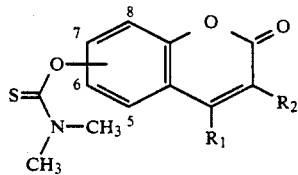

| Position | R₁ | R₂ | M.p. (°C.) |
|---|---|---|---|
| 5 | —CH₃ | —H | 166–168 |
| 7 | —CH₃ | —H | 216 |
| 8 | —CH₃ | —H | 194 |
| 6 | —CH₃ | —H | 164 |
| 7 | —CF₃ | —H | 160 |
| 7 | —CH₃ | —Cl | 184.5 |
| 7 | —CH₂—CH₃ | —H | 158–160 |
| 7 | —CH₂—CH₂—CH₃ | —H | 118–120 |
| 7 (1) | —CH₂—CH₂—CH₂—CH₂— | | 159–160 |

Note: (1) O-(7,8,9,10-tetrahydro-6-oxo-6H-dibenzo[b,d]-pyran-3-yl) dimethylthiocarbamate

TABLE IV

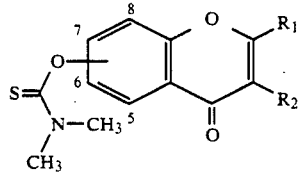

| Position | R₁ | R₂ | M.p. (°C.) |
|---|---|---|---|
| 7 | —CH₃ | —H | 137 |
| 7 | —CH₃ | —CH₃ | 160 |
| 7 | —CH₂—CH₃ | —H | 140 |

TABLE V

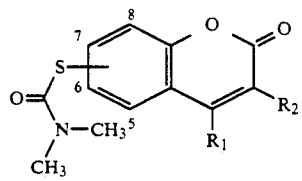

| Position | R₁ | R₂ | M.p. (°C.) |
|---|---|---|---|
| 5 | —CH₃ | —H | 129 |
| 7 | —CH₃ | —H | 154 |
| 8 | —CH₃ | —H | 154 |
| 6 | —CH₃ | —H | 137 |
| 7 | —CF₃ | —H | 138 |
| 7 | —CH₃ | —Cl | 229 |
| 7 | —CH₂—CH₃ | —H | 124 |
| 7 | —CH₂—CH₂—CH₃ | —H | 99–100 |
| 7 (1) | —CH₂—CH₂—CH₂—CH₂— | | 132 |

Note: (1) S-(7,8,9,10-tetrahydro-6-oxo-6H-dibenzo[b,d]-pyran-3-yl) dimethylthiocarbamate

TABLE VI

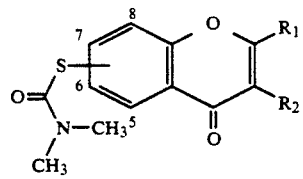

| Position | R₁ | R₂ | M.p. (°C.) |
|---|---|---|---|
| 7 | —CH₃ | —H | 164 |
| 7 | —CH₃ | —CH₃ | 138 |

TABLE VI-continued

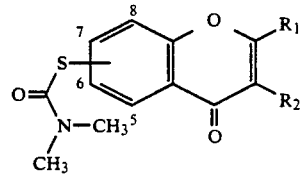

| Position | R₁ | R₂ | M.p. (°C.) |
|---|---|---|---|
| 7 | —CH₂—CH₃ | —H | 116 |

TABLE VII

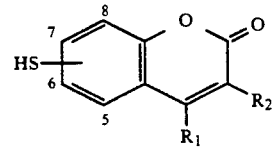

| Position | R₁ | R₂ | M.p. (°C.) |
|---|---|---|---|
| 7 | —CH₃ | —H | 136 |
| 7 | —CH₃ | —H | 132 |
| 8 | —CH₃ | —H | 114–115 |
| 6 | —CH₃ | —H | 138–140 |
| 7 | —CF₃ | —H | 115 |
| 7 | —CH₃ | —Cl | 153 |
| 7 | —CH₂—CH₃ | —H | 152 |
| 7 | —CH₂—CH₂—CH₃ | —H | 88–89 |
| 7 (1) | —CH₂—CH₂—CH₂—CH₂— | | 139 |

Note: (1) 7,8,9,10-tetrahydro-3-mercapto-6H-dibenzo-[b,d]pyran-6-one

TABLE VIII

| POSITION | R₁ | R₂ | M.p. (°C.) |
|---|---|---|---|
| 7 | —CH₃ | —H | 120 |
| 7 | —CH₃ | —CH₃ | 122 |
| 7 | —CH₂—CH₃ | —H | 74 |

What is claimed is:

1. An oside compound selected from the group consisting of the benzopyranone-β-D-thioxylosides of the formula

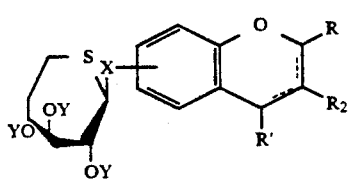

in which:
one of the substituents R or R' is an oxygen atom double-bonded to the corresponding cyclic carbon atom and the other is a group R₁,
the symbol ==== represents a double bond conjugated to the CO group provided by one of the substituents R or R',
X is a sulfur atom or an oxygen atom,
R₁ and R₂, which are identical or different, are each a hydrogen atom, a $C_1$–$C_4$ alkyl group, a halogen atom, a trifluoromethyl group, a phenyl group or $R_1$ and $R_2$ when taken together, form a 7,8,9,10-tetrahydrodibenzo[b,d]pyran-6-one group or a 1,2,3,4-tetrahydro-9H-xanthen-9-one group with the benzopyranone group to which they are bonded, and Y is the hydrogen atom or a $C_2$–$C_5$ aliphatic acyl group.

2. An oside compound according to claim 1, selected from the group consisting of the benzopyran-2-one-β-D-thioxylosides of the formula

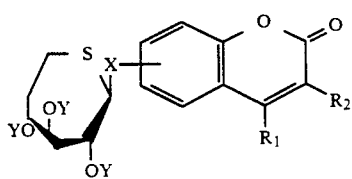

in which:

X is a sulfur atom or an oxygen atom, $R_1$ and $R_2$, which are identical or different, are each a hydrogen atom, a $C_1$–$C_4$ alkyl group, a halogen atom, a trifluoromethyl group, a phenyl group or $R_1$ and $R_2$ when taken together, form a 7,8,9,10-tetrahydrodibenzo[b,d]pyran-6-one group with the benzopyran-2-one group to which they are bonded, and Y is the hydrogen atom or an aliphatic acyl group.

3. An oside compound according to claim 1, selected from the group consisting of the benzopyran-4-one-β-D-thioxylosides of the formula

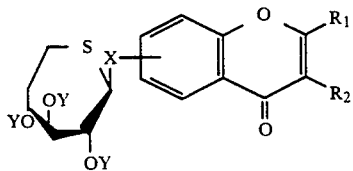

in which:

X is a sulfur atom or an oxygen atom, $R_1$ and $R_2$, which are identical or different, are each a hydrogen atom, a $C_1$–$C_4$ alkyl group, a halogen atom, a trifluoromethyl group, a phenyl group or $R_1$ and $R_2$ when taken together, form a 1,2,3,4-tetrahydro-9H-xanthen-9-one group with the benzopyran-4-one group to which they are bonded, and Y is the hydrogen atom or a $C_2$–$C_5$ aliphatic acyl group.

4. An oside compound according to claim 1 wherein X is bonded in the 7-position to the benzopyranone ring and $R_1$ and $R_2$, which are identical or different, are each a hydrogen atom, a $C_1$–$C_4$ alkyl group, a halogen atom or a phenyl group.

5. An oside compound according to claim 1 wherein Y is the group $CH_3CO$.

6. 4-Methyl-2-oxo-2H-1-benzopyran-7-yl 1,5-dithio-β-D-xylopyranoside.

7. 3-Chloro-4-methyl-2-oxo-2H-1-benzopyran-7-yl 1,5-dithio-β-D-xylopyranoside.

8. 4-Ethyl-2-oxo-2H-1-benzopyran-7-yl 5-thio-β-D-xylopyranoside.

9. A pharmaceutical composition containing, in association with a physiologically acceptable excipient, a therapeutically effective amount to at least one oside compound according to claim 1.

10. A method of treating venous and arterial thrombosis, which comprises administering to a patient in need of such a treatment a compound of formula I according to claim 1 in an amount effective as an antithrombotic.

* * * * *

UNITED STATES PATENT AND TRADEMARK OFFICE
CERTIFICATE OF CORRECTION

PATENT NO. : 5,169,838

DATED : December 8, 1992

INVENTOR(S) : Samreth et al

It is certified that error appears in the above-identified patent and that said Letters Patent is hereby corrected as shown below:

Formula I in abstract, formula I on column I, formulae Ia, Ib on column 2, formula of Table I on column 16, formulae of Tables I (continued) and II on column 17, formula of Table II (continued) on column 18, formula I on column 20 (claim 1), formula Ia on column 21 (claim 2) and formula Ib on column 22 (claim 3), change the 7-membered formulae to

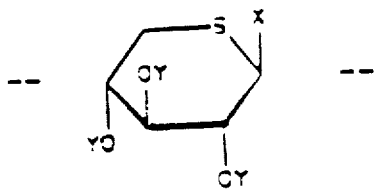

UNITED STATES PATENT AND TRADEMARK OFFICE
CERTIFICATE OF CORRECTION

PATENT NO. : 5,169,838

DATED : December 8, 1992

INVENTOR(S) : Samreth et al

It is certified that error appears in the above-indentified patent and that said Letters Patent is hereby corrected as shown below:

Formula III and IV on column 2 and formula V on column 3, change the 7-membered formulae to

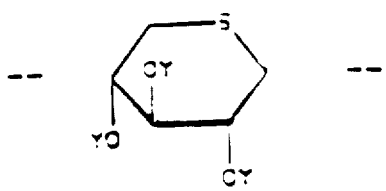

Signed and Sealed this

Twenty-sixth Day of April, 1994

Attest:

BRUCE LEHMAN

Attesting Officer

Commissioner of Patents and Trademarks